United States Patent [19]

Feiler et al.

[11] 4,014,930
[45] Mar. 29, 1977

[54] CARBOXY METHOXY MALONATE

[75] Inventors: William A. Feiler, Kirkwood, Mo.; Norman Earl Stahlheber, Columbia, Ill.

[73] Assignee: Monsanto Company, St. Louis, Mo.

[22] Filed: Dec. 8, 1975

[21] Appl. No.: 638,793

Related U.S. Application Data

[63] Continuation-in-part of Ser. No. 468,713, May 10, 1974, abandoned.

[52] U.S. Cl. .................. 260/535 P; 252/89 R; 252/89 B; 252/132
[51] Int. Cl.² ........................................ C07C 59/23
[58] Field of Search ........................... 260/535 P

[56] References Cited

UNITED STATES PATENTS

| | | | |
|---|---|---|---|
| 3,821,296 | 6/1974 | Blumbergs et al. | 260/535 P |
| 3,904,684 | 9/1975 | Tsuda et al. | 260/535 P |
| 3,914,297 | 10/1975 | Lamberti et al. | 260/535 P |
| 3,925,465 | 12/1975 | Nara et al. | 260/535 P |

*Primary Examiner*—Paul J. Killós
*Attorney, Agent, or Firm*—N. E. Willis; J. E. Maurer; H. B. Roberts

[57] ABSTRACT

A crystalline hydrate of trisodium carboxy methoxy malonate is an effective sequestrant and detergency builder.

2 Claims, No Drawings

CARBOXY METHOXY MALONATE

CROSS REFERENCES TO RELATED APPLICATIONS

This application is a continuation-in-part of U.S. application Ser. No. 468,713 filed May 10, 1974, now abandoned.

BACKGROUND OF THE INVENTION

This invention relates to a novel crystalline hydrate useful as a sequestering agent for metal and alkali earth metal ions and as a builder ingredient in detergent formulations.

It is known that the compound

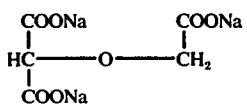

(trisodium carboxy methoxy malonate) is a useful sequestrant and detergency builder. (See, for example, U.S. Pat. No. 3,865,755).

The tendency of the anhydrous amorphous material to adsorb water under conditions of high relative humidity may cause problems in powdered or granular detergent formulations containing the material as a builder. It is additionally known that detergent formulations generally exhibit optimum performance in basic solutions. Therefore, such formulations frequently contain sufficient base to raise the pH of the system in which the formulation is to be employed. The use of additional ingredients such as the base may introduce problems of non-homogeneity of the formulation via settling and stratification of ingredients unless the ingredients are correlated with respect to particle size and density or unless agglomerating procedures are employed to combine the ingredients into composite granules.

Therefore, the desirability of a crystalline relatively non-hygroscopic material possessing the functional characteristics of trisodium carboxy methoxy malonate and being capable of integral compositing with bases will be recognized by those skilled in the art.

SUMMARY OF THE INVENTION

It is an object of this invention to provide a crystalline material possessing the functional characteristics of trisodium carboxy methoxy malonate.

This material is a crystalline hydrate of trisodium carboxy methoxy malonate. The characteristics of this hydrate and methods for its preparation will be understood from the following description of the preferred embodiments.

DESCRIPTION OF THE PREFERRED EMBODIMENTS

The crystalline salt of this invention is a trisodium carboxy methoxy malonate hydrate:

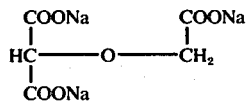

having a characteristic X-ray diffraction pattern measured using a powdered sample and copper $K\alpha_1$ radiation ($\lambda = 1.54050$ A). The X-ray diffraction pattern is characterized by the spacing of strong diffraction lines at the approximate values of the angle $2\theta$: 20.10°, 8.00°, 14.30°, 30.37°, 16.20°, 5.80°, 37.00°, and 10.00° which values of the angle $2\theta$ correspond respectively to the following approximate values of interplanar spacing $d$: 4.414 A, 11.04 A, 6.188 A, 2.941 A, 5.467 A, 15.22 A, 2.428 A, and 8.838 A.

The term "approximate" is used to indicate that the interplanar spacing can vary as much as 1% due to the variations in measurement techniques and possible inclusion of other materials, such as sodium hydroxide, integrally associated with the hydrate crystal.

The phrase "integrally associated" is used herein to indicate that the sodium hydroxide is associated with the trisodium carboxy methoxy malonate hydrate as a double salt, as a solid solution or by crystalline entrapment, or in a similar physically integrated form.

The hydrate is believed to be a dihydrate although the exact amount of water of hydration present is difficult to precisely determine.

The crystalline hydrate of this invention can be prepared by forming an aqueous solution of a mixture of from 80% to 98% by weight trisodium carboxy methoxy malonate (this compound and its preparation and utilities are known from Belgian Pat. No. 785,632, issued Dec. 29, 1972) and, correspondingly, from 2% to 20% by weight sodium hydroxide. Generally, only enough water to dissolve the mixture (usually about 50% by weight of the solution) is utilized.

The crystalline hydrate of this invention can be most conveniently precipitated from this solution by use of a precipitating solvent, for example, acetone, methanol, ethanol, and other organic solvents which are miscible in water. Upon addition of about three volumes of precipitating solvent to one volume of the solution, two liquid phases are formed. The dense phase is a supersaturated solution of the double salt of this invention, which crystallizes from solution on standing. The crystallization process can be accelerated by seeding, and also by repeated washes with the precipitating solvent. The presence of impurities tends to retard precipitation and relatively pure materials are, therefore, preferably utilized.

The sodium hydroxide is integrally composited with the hydrate crystalline structure to provide a builder of high basicity. If desired, however, NaOH can be removed, washing the product with methanol.

The hydrate of this invention can be used in detergent formulations as a builder in the same manner as trisodium carboxy methoxy malonate, advantageously adding additional basicity to the formulation.

The detergent formulations will contain at least 1% by weight, and preferably at least 5% by weight, of the hydrate of this invention. In order to obtain the maximum advantages of the builder compositions of this invention, the use of from 5% to 75% of this double salt is particularly preferred. The hydrate compound of this invention can be the sole detergency builder or this compound can be utilized in combination with other detergency builders which may constitute from 0 to 95% by weight of the total builders in the formulation.

By way of example, builders which can be employed in combination with the novel builder compounds of this invention include water soluble inorganic builder salts such as alkali metal polyphosphates, i.e., the tripolyphosphates and pyrophosphates, alkali metal carbonates, borates, bicarbonates and silicates and water soluble organic builders including amino polycarboxylic acids and salts such as alkali metal nitrilotriacetates, cycloalkane polycarboxylic acids and salts, other ether polycarboxylates, such as tetrasodium carboxymethyloxysuccinate and trisodium carboxy methoxy malonate, alkyl polycarboxylates, epoxy polycarboxylates, tetrahydrofuran polycarboxylates such as 1,2,3,4 or 2,2,5,5 tetrahydrofuran tetracarboxylates, benzene polycarboxylates, oxidized starches, amino (trimethylene phosphonic acid) and its salts, diphosphonic acids and salts (e.g., methylene diphosphonic acid; 1-hydroxy ethylidene diphosphonic acid), and the like.

The detergent formulations will generally contain from 5% to 95% by weight total builder (although greater or lesser quantities may be employed if desired) which, as indicated above, may be solely the hydrate compound of this invention or mixtures of such compound with other builders. The total amount of builder employed will be dependent on the intended use of the detergent formulation, other ingredients of the formulation, pH conditions, and the like. For example, general laundry powder formulations will usually contain 20% to 60% builder; liquid dishwashing formulations 11% to 12% builder; machine dishwashing formulations 60% to 90% builder. Optimum levels of builder content as well as optimum mixtures of builders of this invention with other builders for various uses can be determined by routine tests in accordance with conventional detergent formulation practice.

The detergent formulations will generally contain a water soluble detergent surfactant, although the surfactant ingredient may be omitted from machine dishwashing formulations. Any water soluble anionic, nonionic, zwitterionic or amphoteric surfactant can be employed.

Examples of suitable anionic surfactants include soaps such as the salts of fatty acids containing about 9 to 20 carbon atoms, linear alkyl benzene sulfonates in which the alkyl group contains from 10 to 16 carbon atoms; alcohol sulfates; ethoxylated alcohol sulfates; hydroxy alkyl sulfonates; alkyl sulfates and sulfonates; olefin sulfonates; alkenyl sulfonates; monoglyceride sulfates; acid condensates of fatty acid chlorides with hydroxy alkyl sulfonates and the like.

Examples of suitable nonionic surfactants include alkylene oxide (e.g., ethylene oxide), condensates of mono- and polyhydroxy alcohols, alkyl phenols, fatty acid amides, and fatty amines; amine oxides; sugar derivatives such as sucrose monopalmitate; long chain tertiary phosphine oxides; dialkyl sulfoxides; fatty acid amides, (e.g., mono- or diethanol amides of fatty acids containing 10 to 18 carbon atoms), and the like.

Examples of suitable zwitterionic surfactants include derivatives of aliphatic quaternary ammonium compounds such as 3-(N,N-dimethyl-N-hexadecylammonio)propane-1-sulfonate and 3-(N,N-dimethyl-N-hexadecylammonio)-2-hydroxy propane-1-sulfonate.

Examples of suitable amphoteric surfactants include betains, sulfobetains and fatty acid imidazole carboxylates and sulfonates.

It will be understood that the above examples of surfactants are by no means comprehensive and that numerous other surfactants are known to those skilled in the art. It will be further understood that the choice and use of surfactants will be in accordance with well-understood practices of detergent formulations. For example, anionic surfactants, particularly linear alkyl benzene sulfonate, are preferred for use in general laundry formulations; whereas low foaming nonionic surfactants are preferred for use in machine dishwashing formulations.

The quantity of surfactant employed in the detergent formulations will depend on the surfactant chosen and the end use of the formulation. In general, the formulations will contain from 5% to 50% surfactant by weight, although as much as 95% or more surfactant may be employed if desired. For example, general laundry powder formulations normally contain 5% to 50%, preferably 15% to 25%, surfactant; machine dishwashing formulations 0.5% to 5%; liquid dishwashing formulations 20% to 45%. The weight ratio of surfactant to builder will generally be in the range of from 1:12 to 2:1.

In addition to builder and surfactant components, detergent formulations may contain fillers such as sodium sulfate and minor amounts of bleaches, dyes, optical brighteners, soil anti-redeposition agents, perfumes and the like.

In machine dishwashing compositions the surfactant will be a low-foaming nonionic or anionic, preferably nonionic surfactant which will constitute 0 to 5% of the formulation.

The term "low-foaming" surfactant connotes a surfactant which, in the foaming test described below, reduces the revolutions of the washer jet-spray arm during the wash and rinse cycles less than 15%, preferably less than 10%.

In the foaming test, 1.5 grams of surfactant is added to a 1969 Kitchen-Aid Home Dishwasher, Model No. KOS-16, manufactured by Hobart Manufacturing Company, which is provided with means for counting revolutions of the washer jet-spray arm during wash and rinse cycles. The machine is operated using distilled water feed at a machine entrance temperature of 40° C. The number of revolutions of the jet-spray arm during the wash and rinse cycles is counted. The results are compared with those obtained by operation of the machine using no surfactant charge, and the percentage decrease in number of revolutions is determined.

The surfactant should, of course, be compatible with the chlorine-containing component hereinafter discussed. Examples of suitable nonionic surfactants include ethoxylated alkyl phenols, ethoxylated alcohols (both mono- and dihydroxy alcohols), polyoxyalkylene glycols, aliphatic polyethers and the like. The widely commercially utilized condensates of polyoxypropylene glycols having molecular weights of from about 1400 to 2200 with ethylene oxide (the ethylene oxide constituting 5 to 35 weight percent of the condensate) are, for example, advantageously used in the machine dishwashing formulations of this invention.

Suitable low-foaming anionic surfactants include alkyldiphenyl ether sulfonates such as sodium dodecyl diphenyl ether disulfonates and alkyl naphthalene sulfonates.

Mixtures of suitable low-foaming surfactants can be utilized if desired.

In addition, machine dishwashing formulations will contain sufficient chlorine providing compound to provide 0.5% to 2% available chlorine. For example, the formulation may contain from 0.5% to 5%, preferably 1% to 3%, of a chlorocyanurate or from 10% to 30% chlorinated trisodium phosphate. Suitable chlorocyanurates are sodium and potassium dichlorocyanurate; [(monotrichloro)tetra-(monopotassium dichloro)] penta-isocyanurate; (monotrichloro)(monopotassium dichloro) diisocyanurate.

Machine dishwashing compositions should additionally contain from 5% to 30% soluble sodium silicate having an $SiO_2$ to $Na_2O$ mole ratio of from 1:1 to 3.2:1, preferably about 2.4:1, to inhibit corrosion of metal parts of dishwashing machines and provide over-glaze protection to fine china.

Machine dishwashing compositions will generally contain at least 10%, preferably at least 20%, builder; up to a maximum of about 90% builder. The new builder compounds of this invention should constitute at least 5% of the weight of the machine dishwashing formulation in order to obtain the full effects of their inherent characteristics.

The invention is further illustrated by the following example wherein all parts and percentages are by weight unless otherwise indicated.

EXAMPLE I

An aqueous solution containing 708 grams of trisodium carboxy methoxy malonate in one liter of water is treated with 240 grams of 50% aqueous sodium hydroxide. This solution is cooled to 30° C. and 3 liters of acetone is added with vigorous stirring.

The mixture is allowed to settle and the supernatant layer containing acetone, water, a small amount of sodium hydroxide (amounting to about 5% of the total sodium hydroxide) and trisodium carboxy methoxy malonate is discarded. The denser layer is washed with two equal volumes of acetone, whereupon crystalline product forms. The product is dried at 50° C. and milled to a powder.

The powder is a crystalline hydrate exhibiting the X-ray diffraction pattern shown below. (The pattern is determined using the powdered sample and copper $K\alpha_1$ radiation) which is different from the diffraction patterns of crystalline anhydrous trisodium carboxy methoxy malonate and crystalline sodium hydroxide.

| $2\theta$ | d,A | $I/I_o$ |
| --- | --- | --- |
| 20.1 | 4.414 | 100 |
| 8.00 | 11.04 | 90 |
| 14.30 | 6.188 | 80 |
| 30.37 | 2.914 | 80 |
| 16.20 | 5.467 | 70 |
| 5.80 | 15.22 | 30 |
| 10.00 | 8.838 | 40 |
| 37.00 | 2.428 | 40 |

What is claimed is:

1. A crystalline hydrate of trisodium carboxy methoxy malonate having a copper $K\alpha$ X-ray diffraction pattern characterized by strong diffraction lines at the approximate values of the angle $2\theta$: 20.10°, 8.00°, 14.30°, 30.37°, 16.20°, 5.80°, 37.00°, and 10.00°, said values of the angle $2\theta$ corresponding, respectively, to the values of interplanar spacing d: 4.414 A, 11.04 A, 6.188 A, 2.941 A, 5.467 A, 15.22 A, 2.428 A, and 8.838 A.

2. A method of making a crystalline hydrate of trisodium carboxy methoxy malonate having a copper $K\alpha$ X-ray diffraction pattern characterized by strong diffraction lines at the approximate values of the angle $2\theta$: 20.10°, 8.00°, 14.30°, 30.37°, 16.20°, 5.80°, 37.00°, and 10.00°, said values of the angle $2\theta$ corresponding, respectively, to the values of interplanar spacing d: 4.414 A, 11.04 A, 6.188 A, 2.941 A, 5.467 A, 15.22 A, 2.428 A, and 8.838 A, said method comprising forming an aqueous solution of a mixture of from 80% to 98% by weight trisodium carboxymethoxy malonate and, correspondingly, from 20% to 2% sodium hydroxide and precipitating said crystalline hydrate from said solution.

* * * * *